(12) United States Patent
Elmen

(10) Patent No.: US 10,596,332 B2
(45) Date of Patent: Mar. 24, 2020

(54) DEVICE FOR ADJUSTING NEEDLE INSERTION DEPTH

(71) Applicant: Carebay Europe Ltd., Swatar (MT)

(72) Inventor: Gunnar Elmen, Huddinge (SE)

(73) Assignee: SHL MEDICAL AG, Zug (CH)

( * ) Notice: Subject to any disclaimer, the term of this patent is extended or adjusted under 35 U.S.C. 154(b) by 58 days.

(21) Appl. No.: 15/307,318

(22) PCT Filed: Apr. 10, 2015

(86) PCT No.: PCT/EP2015/057824
§ 371 (c)(1),
(2) Date: Oct. 27, 2016

(87) PCT Pub. No.: WO2015/165717
PCT Pub. Date: Nov. 5, 2015

(65) Prior Publication Data
US 2017/0043105 A1 Feb. 16, 2017

(30) Foreign Application Priority Data

Apr. 29, 2014 (SE) ...................................... 1450508

(51) Int. Cl.
*A61M 5/46* (2006.01)
*A61M 5/32* (2006.01)

(52) U.S. Cl.
CPC ............ *A61M 5/46* (2013.01); *A61M 5/3204* (2013.01); *A61M 2205/581* (2013.01); *A61M 2205/582* (2013.01); *A61M 2205/583* (2013.01)

(58) Field of Classification Search
CPC .................. A61M 5/46; A61M 5/3204; A61M 2205/581; A61M 2205/582; A61M 2205/583; A61J 7/04
See application file for complete search history.

(56) References Cited

U.S. PATENT DOCUMENTS

| | | | | | |
|---|---|---|---|---|---|
| 5,226,895 | A | * | 7/1993 | Harris | A61J 1/1406 604/208 |
| 5,599,309 | A | * | 2/1997 | Marshall | A61M 5/2033 604/117 |
| 5,944,700 | A | * | 8/1999 | Nguyen | A61M 5/46 604/117 |
| 8,591,463 | B1 | * | 11/2013 | Cowe | A61M 5/20 604/117 |

(Continued)

FOREIGN PATENT DOCUMENTS

WO 2014/029621 A1 2/2014

*Primary Examiner* — Nilay J Shah
(74) *Attorney, Agent, or Firm* — McDonnell Boehnen Hulbert & Berghoff LLP

(57) ABSTRACT the present invention relates to a device for a medicament delivery device, which extends along a longitudinal axis and comprises a medicament delivery member cover (18) arranged at a proximal end thereof; wherein the device comprises a delivery member protruding adjuster (28) operably connected to said medicament delivery member cover (18). The invention is characterised in that the device further comprises a signal generating mechanism (34) operably connected to said delivery member protruding adjuster (28) and arranged to provide an audible and/or tactile and/or visual signal indicating that a certain penetration depth has been set.

17 Claims, 8 Drawing Sheets

(56) References Cited

U.S. PATENT DOCUMENTS

| | | | |
|---|---|---|---|
| 2007/0265576 A1* | 11/2007 | Pessin | A61M 5/3202 604/198 |
| 2010/0324485 A1 | 12/2010 | Cowe | |
| 2012/0035538 A1* | 2/2012 | Elmen | A61M 5/2459 604/89 |
| 2012/0283647 A1* | 11/2012 | Cronenberg | A61M 5/31595 604/207 |
| 2015/0141929 A1* | 5/2015 | Fabien | A61M 5/2033 604/198 |

* cited by examiner

DEVICE FOR ADJUSTING NEEDLE INSERTION DEPTH

CROSS-REFERENCE TO RELATED APPLICATIONS

The present application is a U.S. National Phase Application pursuant to 35 U.S.C. § 371 of International Application No. PCT/EP2015/057824 filed Apr. 10, 2015, which claims priority to Swedish Patent Application No. 1450508-5 filed Apr. 29, 2014. The entire disclosure contents of these applications are herewith incorporated by reference into the present application.

TECHNICAL AREA

The present invention relates to a device to be incorporated in a medicament delivery device, which is arranged with a mechanism for adjusting a delivery member protruding length.

BACKGROUND OF INVENTION

Many devices for administering a medicament are designed with a number of functions for providing ease of use for self-administration. The functions that are applicable comprise mixing of the medicament with a diluent, if the medicament is in powder form, priming of the medicament container, thereby reducing any air trapped therein, penetration of an injection needle into the tissue of a patient on an injection site, injection of a dose of medicament at the injection site, withdrawal of the injection needle after ended injection sequence and covering of the injection needle after use of the medicament delivery device.

Some medicament delivery devices require that a delivery member protrudes a certain length from the proximal end of the device when expelling a medicament through the delivery member. When using injection devices, some types of medicament require that the dose is injected at a certain depth into the tissue of the patient. Depending on the type of drug and/or treatment, the injection depth could be any of superficial, subcutaneous to intramuscular. In that respect, the injection depth also depends on the condition of the patient, i.e. the amount of fat in the subcutaneous tissue. Because of the demands on the penetration depth of the injection, devices have been developed that are arranged with mechanisms that can adjust the penetration depth.

The patent application No. PCT/EP2013/066542 discloses a medicament delivery device that is arranged with a needle shield arranged slidable in a longitudinal direction of the device. The proximal end of the needle shield is intended to be pressed against an injection site, whereby it slides in the distal direction, causing a penetration. The penetration stops when the needle shield hits a stop ledge or an abutment. In order to alter the penetration depth, the proximal end of the needle shield is provided with a penetration depth adjusting mechanism. It comprises a generally tubular part, a delivery member protruding adjuster, arranged with threads on its inner surface, arranged to cooperate with corresponding threads on the outer proximal surface area of the needle shield.

Thus, when the delivery member protruding adjuster is rotated in relation to the needle shield the penetration depth can be adjusted. In order for a user to be able to know the set depth, the outer surface of the needle shield is arranged with indicia such as numbers, for instance indicating penetration depth in millimetres. The indicia are then intended to cooperate with a marking or a cut-out on a distally directed end area of the delivery member protruding adjuster such that when the indicia and the marking are aligned, the depth indicated by the indicia has been set.

However, apart from the visual signs on the device it is sometimes difficult for a user to be sure that the proper penetration depth has been actually set. Also, there is a risk that the delivery member protruding adjuster is rotated accidentally prior to injection, causing the penetration depth to be altered. There is thus room for improvements in the area of penetration depth adjusting mechanisms for medicament delivery devices.

BRIEF DESCRIPTION OF INVENTION

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices. This aim is obtained by a device for a medicament delivery device comprising the features of the independent patent claim 1. Preferable features and/or embodiments of the invention form the subject of the dependent patent claims.

The device according to the present invention is intended to be used with a medicament delivery device, which medicament delivery device extends along a longitudinal axis and comprises a medicament delivery member cover arranged at a proximal end thereof. The medicament delivery device may be arranged to accommodate a suitable medicament container and a delivery member e.g. an injection needle. The medicament delivery device may further be arranged with different types of drive mechanisms that are capable of expelling doses of medicament from the medicament container through the delivery member as well as actuation mechanisms that are capable of performing different functions such as in e.g. in injection devices performing penetration and/or withdrawal of an injection needle, protection of the injection needle before and/or after dose delivery etc. The device according to the present invention is not limited to any specific type of medicament delivery device of a specific function other than to a delivery member protruding length adjusting mechanism that generates an audible and/or tactile and/or visual signal indicating that a certain delivery member protruding length has been set.

In that respect, the device may comprise a delivery member protruding adjuster operably connected to said medicament delivery member cover for adjusting the required or desired delivery member protruding length, e.g. penetration depth, for a particular medicament to be delivered.

According to a main aspect of the present invention, the device comprises a signal generating mechanism arranged between the delivery member protruding adjuster and the medicament delivery member cover such that when the delivery member protruding adjuster is moved in relation to the medicament delivery member cover an audible and/or tactile and/or visual signal is generated for indicating that a certain delivery member protruding length has been set e.g. a certain penetration depth has been set. With this solution, it is ascertained that e.g. a user of an injection device is provided with a positive and distinct indication that a certain penetration depth has been set. There is thus no uncertainty regarding the position of the delivery member protruding adjuster.

According to a feasible solution, the signal generating mechanism comprises first signal elements arranged on the medicament delivery member cover and second signal elements arranged on the delivery member protruding adjuster such that the first and second signal elements will interact with each other when displacement of said delivery member protruding adjuster in relation to said medicament delivery member cover and thereby providing an audible and/or tactile and/or visual signal.

According to a feasible solution, the delivery member protruding adjuster may be provided with threads, which are designed to interact with threads on said medicament delivery member cover such that turning of said delivery member protruding adjuster in relation to said medicament delivery member cover will alter the delivery member protruding length e.g. in an injection device it will alter the penetration depth. The use of threads provides an easy, reliable and intuitive way of setting a certain delivery member protruding length or penetration depth with very few components.

In that respect, the first signal elements may comprise at least one flexing element flexible in a direction generally perpendicular to the longitudinal axis. Preferably the first signal element may further comprise at least one protrusion and said second signal element comprises a number of recesses. This provides the function, when the at least one protrusion is moved in position with one of the recesses, the flexing element will cause a sudden movement of the at least one protrusion into said recess, casing an impact, thereby providing a signal. The advantage is that the flexing properties of the material will enable the movement and thereby the generation of the signal.

In order to provide a distinct signal, the second signal elements may comprise a number of recesses where each recess corresponds to a certain delivery member protruding length. Further, according to a feasible solution, the delivery member protruding adjuster may comprise indicia indicative to a certain delivery member protruding length. In addition to the signal, this will also give the user a visual indication of the delivery member protruding length set.

Further, the medicament delivery member cover together with the delivery member protruding adjuster are movable, more particularly linearly movable, in relation to the housing from a first position in which the delivery member is surrounded by the medicament delivery member cover or by both the medicament delivery member cover and the delivery member protruding adjuster, to a second position in which the delivery member protrudes or is caused to protrude a certain length measured from the proximal end of the delivery member protruding adjuster.

According to a further feature of the invention, it may comprise a tool operably connectable to said delivery member protruding adjuster for adjusting the delivery member protruding length e.g. the penetration depth in an injection device. This is an advantage for users with poor dexterity in their hands. The tool may be designed to facilitate rotation of the delivery member protruding adjuster. Preferably, the tool and the delivery member protruding adjuster are arranged with form-locking elements in order to transfer rotational movement from the tool to the delivery member protruding adjuster.

In that respect, the tool may be arranged connectable to a central passage of said delivery member protruding adjuster, wherein the tool and the passage are arranged with cooperating rotation locking elements, which rotation locking elements are designed to allow longitudinal movement between said tool and said delivery member protruding adjuster.

In addition to the adjusting function of the tool it may also be provided with gripping elements for gripping a delivery member shield surrounding a delivery member placed inside the medicament delivery device, wherein the delivery member shield may be removed when the tool is pulled from the delivery member protruding adjuster. With this feature, the tool then acts as both an adjuster as well as a removing element. In the case that the delivery member is a needle and the delivery member shield is a needle shield, then the needle shield may be any type that is available on the market, such as rigid needle shields (RNS) or flexible needle shields (FNS). The gripping elements then are modified to handle a specific type of needle shield.

In order to enhance the fitting of the tool inside the delivery member protruding adjuster and said medicament delivery member cover and in order to reduce the risk of unintentional falling out of the tool from the proximal end of the device, the tool may be arranged with friction enhancing element arranged to interact with the delivery member protruding adjuster and/or said medicament delivery member cover for holding said tool.

These and other aspects and advantages of the present invention will become apparent from the following detailed description of the invention and from the accompanying drawings.

BRIEF DESCRIPTION OF DRAWINGS

In the following detailed description of the invention, reference will be made to the accompanying drawings, of which.

DETAILED DESCRIPTION OF THE INVENTION

Figure 1:
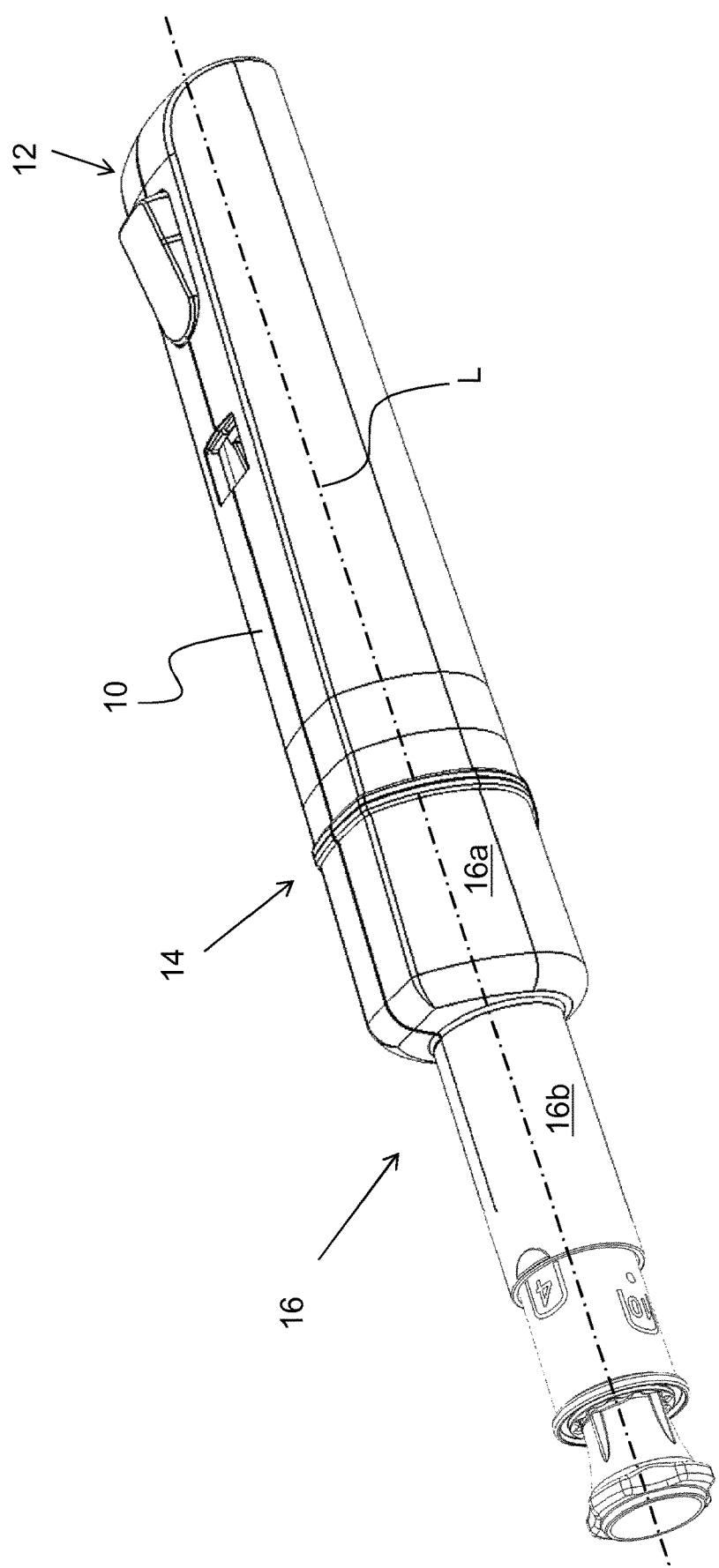
FIG. 1 is a perspective view of a medicament delivery device comprising a device according to the present invention.

The embodiment shown in the drawings comprises a generally elongated main housing 10 having a distal end 12 and a proximal end 14, FIG. 1. At the proximal end 14 a proximal housing part 16 is arranged to be releasibly attached to the main housing 10 with a first tubular part 16a, having generally the same diameter as the main housing 10. Attaching elements could comprise threads, bayonet connections, snap-in elements and the like. In the embodiment shown, the attaching elements are bayonet connections, as will be described below. The first tubular part 16a is arranged to a second tubular part 16b having a lesser diameter than the first tubular part 16a. In the embodiment shown, the two housing parts 16a, 16b are separate components that are attached to each other in a suitable manner.

The main housing 10 may further comprise a drive mechanism, an activation mechanism and the like that are capable of performing different functions that are normal for medicament delivery device, such as penetration, dose delivery, withdrawal, etc. These functions may be manually activated or automatically activated depending on the desired level of functionality. These functions and the corresponding technical features do not form part of the invention and will therefore not be described in any detail.

Figure 2:
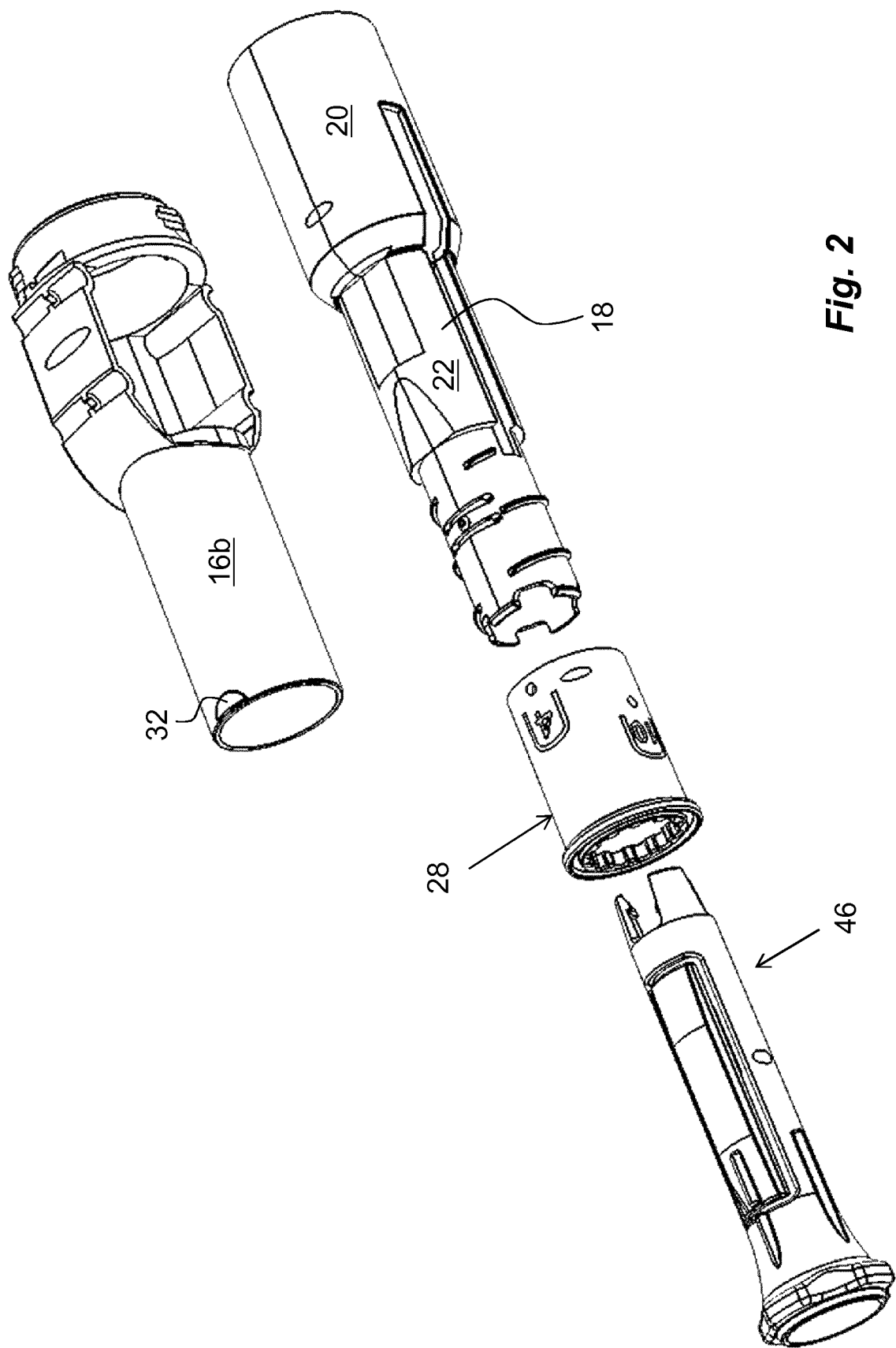
FIG. 2 is an exploded view of a device according to the present invention.

The medicament delivery device is preferably arranged with a medicament delivery member cover 18, FIG. 2. The medicament delivery member cover 18 is arranged with a distal tubular part 20, which transforms into a proximal tubular part 22. The outer diameter of the proximal tubular part 22 is somewhat smaller than the second tubular part 16b of the proximal housing part 16 such that the medicament delivery member cover 18 can move in the longitudinal direction L in relation to the proximal housing part 16. The medicament delivery member cover 18 is further arranged rotatably locked in relation to the medicament delivery device by appropriate mechanisms. These are not shown since they do not form part of the invention.

Figure 3:
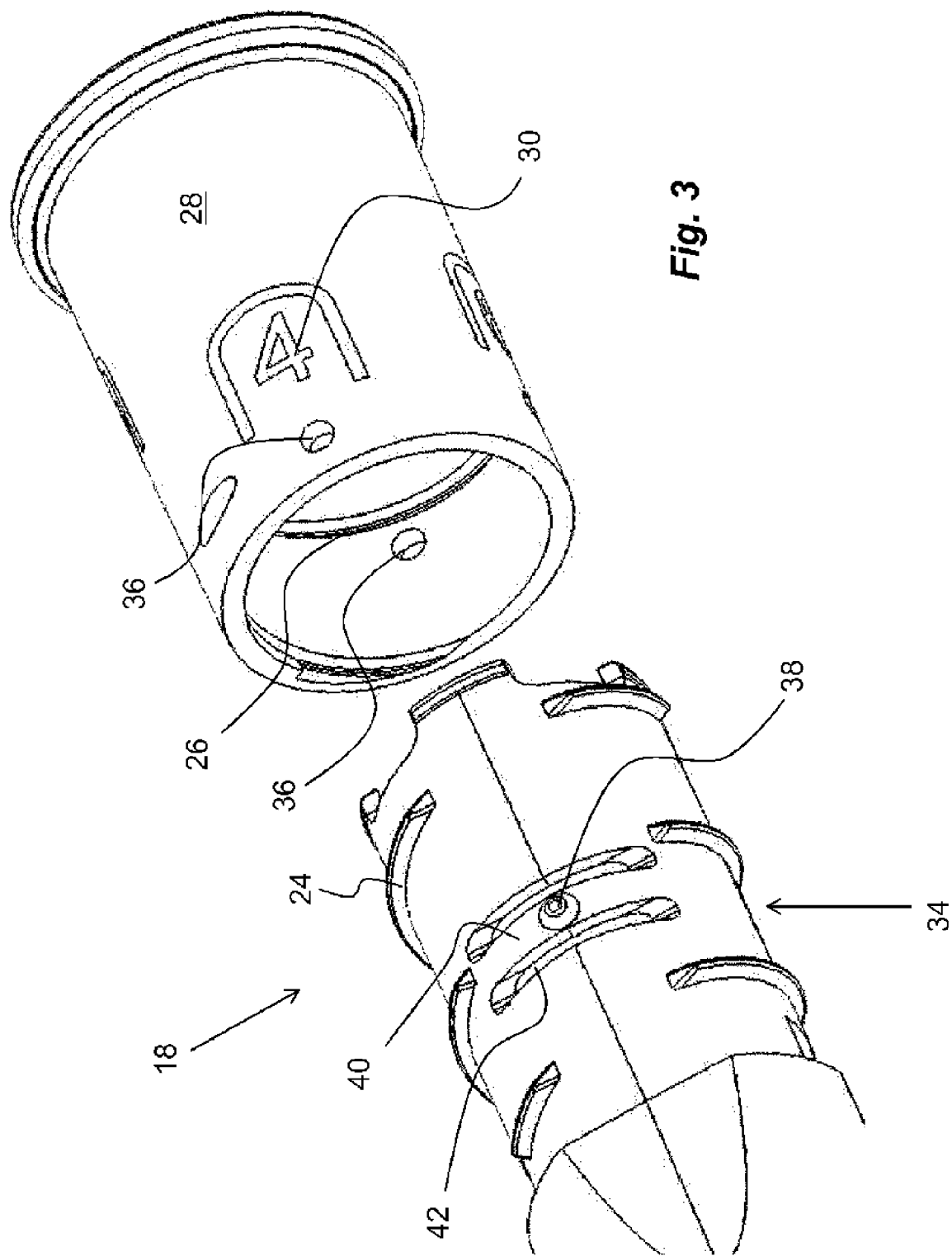
FIGS. 3-8 are detailed views of components and elements comprised in a device according to the present invention.
Figure 4:
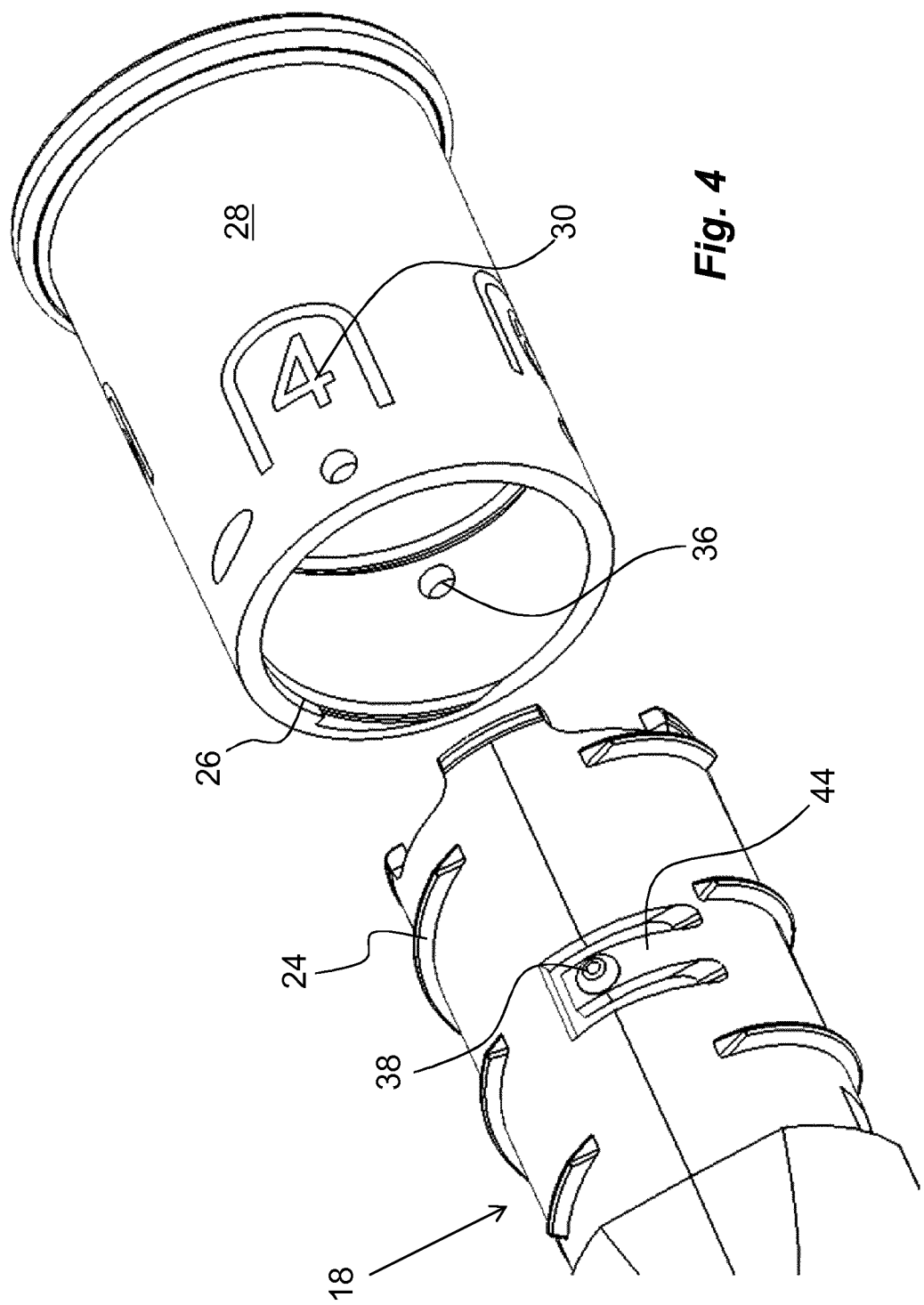

An outer surface of the medicament delivery member cover 18 is arranged with threads 24, FIGS. 3 and 4, which threads 24 are arranged to cooperate with corresponding threads 26, FIGS. 3 and 4, on an inner surface of a generally tubular element 28, hereafter named delivery member protruding adjuster. The outer surface of the delivery member protruding adjuster 28 is arranged with indicia 30, such as numbers. These indicia 30 are to cooperate with a marking 32, FIG. 2, in the proximal end of the second tubular part 16b. Thus, the delivery member protruding adjuster 28 is turned in relation to the medicament delivery member cover 18 for setting a desired protruding length of the delivery member measured from the proximal end of the delivery member protruding adjuster e.g. a desired penetration depth of an injection needle, which penetration depth may vary due to the type of medicament and treatment scheme.

According to the embodiment shown, a signal generating mechanism 34 is arranged for positively and surely indicating to a user that a certain protruding length of the delivery member measured from the proximal end of the delivery member protruding adjuster, e.g. penetration depth, has been set.

The signal generating mechanism 34 comprises first signal elements arranged on the medicament delivery member cover and second signal elements arranged on the delivery member protruding adjuster. The first signal elements comprise at least one flexing element flexible in a direction generally perpendicular to the longitudinal axis and the second signal elements are a number of recesses 36, passages or cut-outs of a certain size which are positioned in relation to the indicia 30 shown on the delivery member protruding adjuster 28. In the present embodiment, the at least one flexing element is configured as a bridge or land 40, FIG. 3, that is created by two parallel elongated cut-outs 42, creating an elongated bridge 40 that extends in the generally circumferential direction. Further, a protrusion 38 is arranged on the bridge or land 40. The recesses are arranged to interact with the protrusion 38 comprised in the signal generating mechanism, having a size that fits into the recesses 36. The bridge 40 will then have a certain flexibility in the radial direction such that the bridge 40 flexes radially inwards when the protrusion 38 is in contact with the inner surface of the delivery member protruding adjuster 28.

Figure 5:
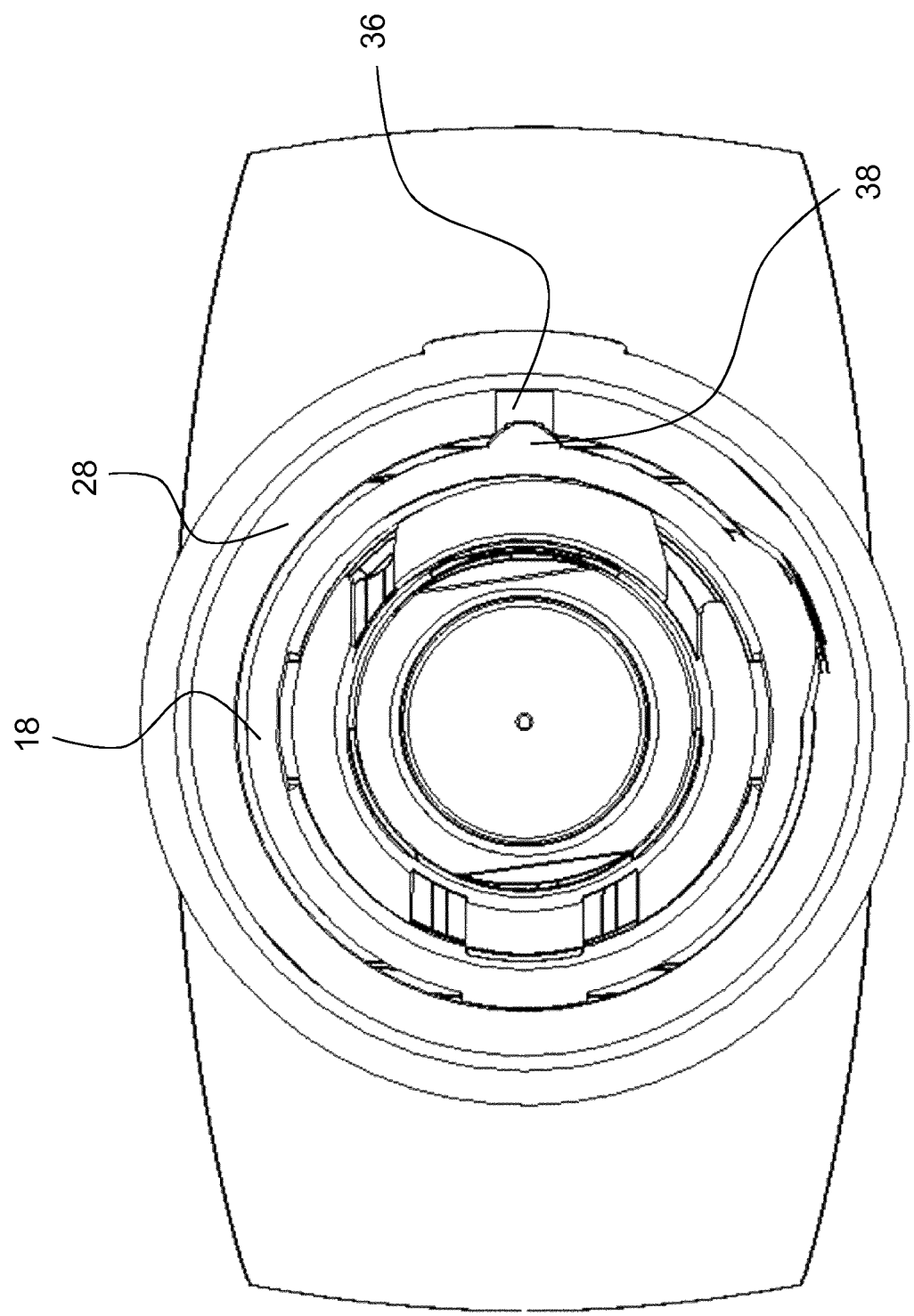

When the protrusion 38 is moved in position with a recess 36, it will then rapidly flex radially outwards and due to the sudden impact of the protrusion 38 in the recess 36, a signal is generated, which may be both tactile as well as audible. In order to increase the strength of the signal, the protrusion in the embodiment shown is designed as a truncated cone as seen in FIG. 5, and the recesses 36 are arranged as circular passages with straight side surfaces. Thus, when the cone-shaped protrusion 38 is moved in position with a passage 36, the inclined walls of the cone 38 will hit the circular inner edge of the passage 36 with a certain speed and force, providing the tactile and audible signal to the user that a certain depth has been set, which is shown by the indicia 30 assigned to that passage being in position adjacent the marking as seen in FIG. 1, where the indicia "4" is adjacent the marking.

It is to be understood that the protrusion 38 and the recesses 36 may have a number of different shapes in order to provide the desired signal. Also, the flexible bridge 40 may be replaced with other flexible structures such as e.g. a tongue 44, FIG. 4, having a free end that is flexible in the radial direction, which free end is provided with the protrusion 38. Further, if a passage 36 is used as shown in the embodiment that goes through the wall of the delivery member protruding adjuster, the protrusion 38 will then be visible in the passage 36 when in the proper position. In that respect, the protrusion 38 may have a distinctive colour that is clearly indicative, providing a further signalling feature which depth has been set.

The delivery member protruding adjuster 28 may be turned by hand by merely gripping on the circumference of the delivery member protruding adjuster 28 and to turn it in relation to the medicament delivery member cover 18 in order to set a desired a protruding length of the delivery member measured from the proximal end of the delivery member protruding adjuster, e.g. penetration depth, e.g. a desired penetration depth. As an alternative, or in addition, the delivery member protruding adjuster 28 may be turned by a special tool. In the embodiment shown, a delivery member shield remover 46 is included, FIG. 6. It comprises an elongated body 48 provided with a gripping knob 50 at its proximal end. The diameter of the elongated body 48 is somewhat smaller than a central passage 52, FIG. 6, at the proximal end of the delivery member protruding adjuster 28 so that the delivery member shield remover 46 may be introduced into both the delivery member protruding adjuster 28 and the medicament delivery member cover 18.

Figure 7:
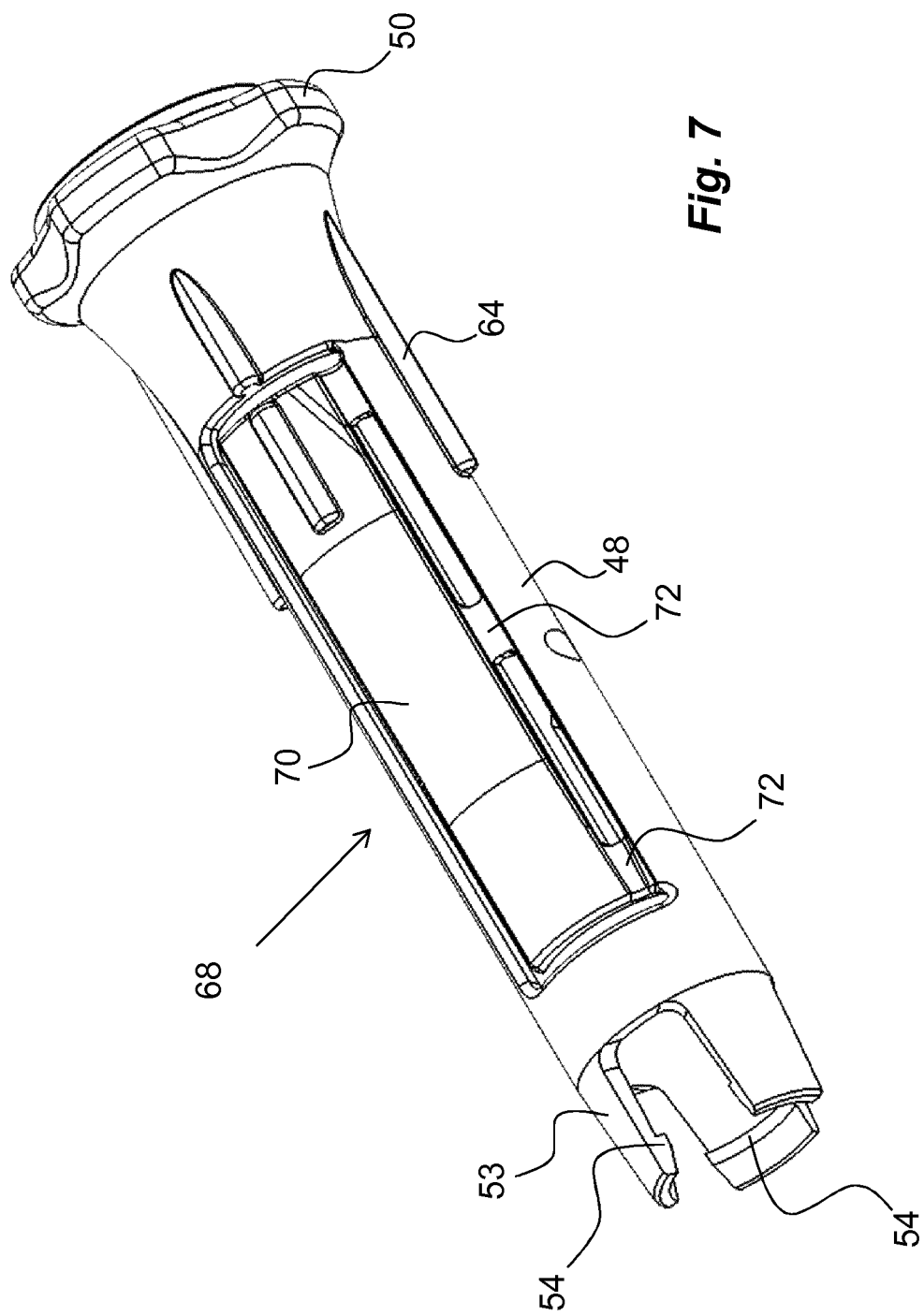
Figure 8:
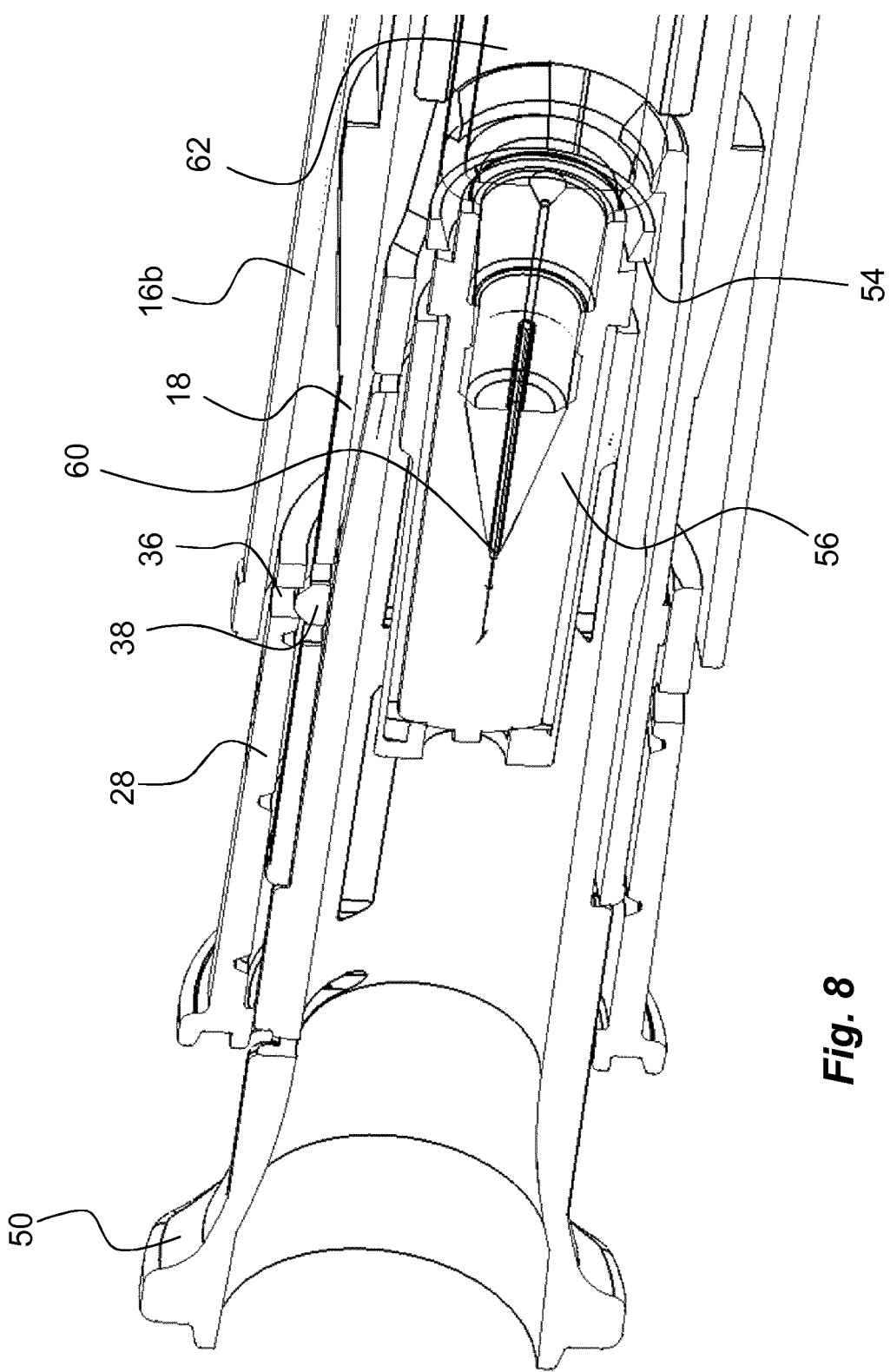

The delivery member shield remover 46 is further arranged with distally directed arms 53, FIG. 7, at its distal end. The arms 53 are arranged with generally radially inwardly directed ledges 54. When the delivery member shield remover 46 is introduced into the delivery member protruding adjuster 28 and the medicament delivery member cover 18, the arms 53 will come in contact with a delivery member shield 56, FIG. 8, arranged protecting the delivery member 60 e.g. an injection needle, in turn connected to a medicament container 62. The contact will cause the arms 53 to flex outwards whereby the inwardly directed ledges 54 slide along the outer surface of the delivery member shield 56 to the distal end of the delivery member shield, at which position the arms 53 and the ledges 54 will flex radially inwards, whereby the ledges 54 will be positioned in contact with the distally directed end wall of the delivery member shield 56 as seen in FIG. 8.

Figure 6:
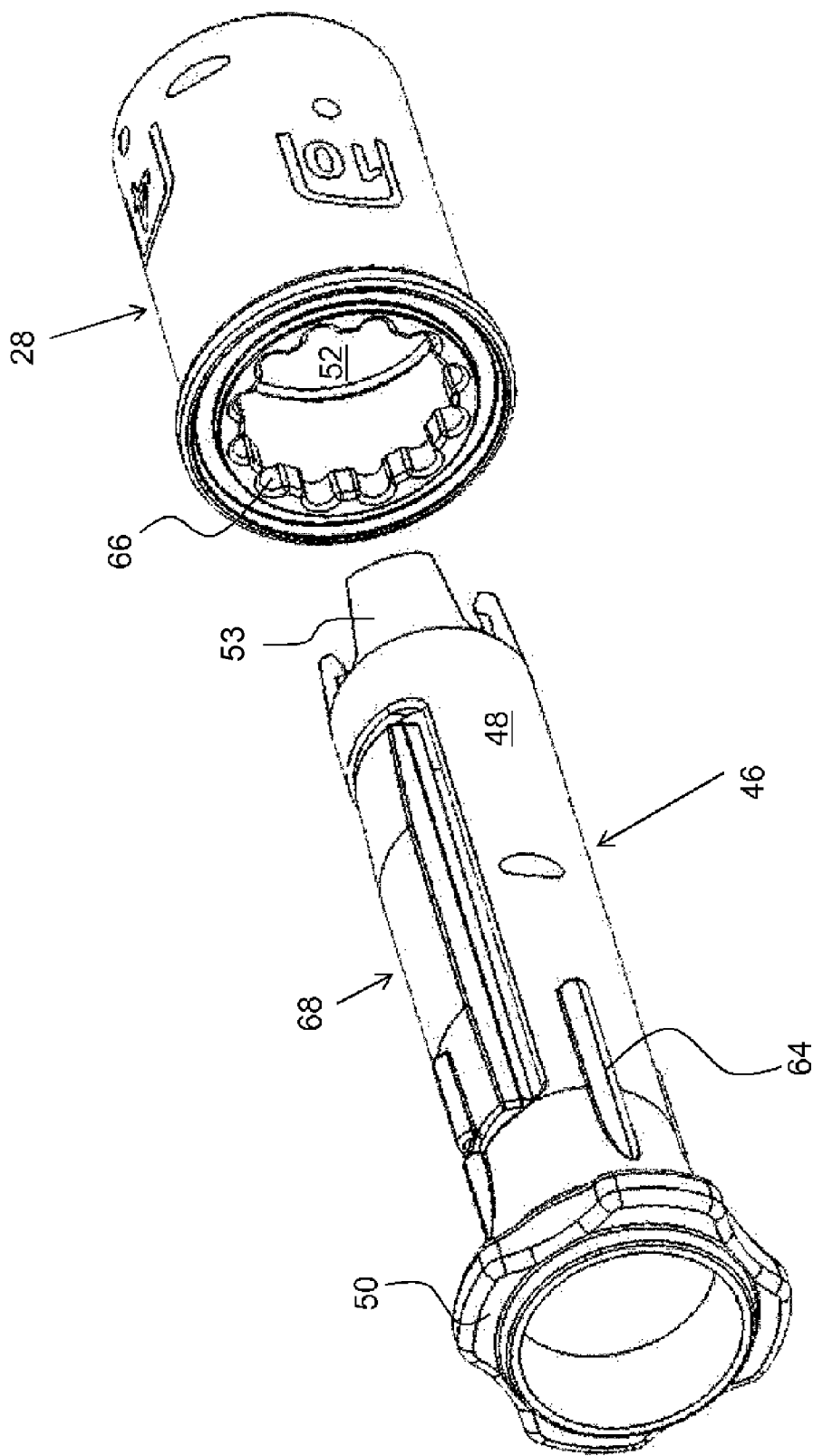

The outer surface of the elongated body 48 of the delivery member shield remover 46 is provided with a number of longitudinally extending ledges 64, FIGS. 6 and 7.

These ledges 64 fit into correspondingly shaped recesses 66 arranged around the circumferential edge of the central passage 52 of the delivery member protruding adjuster 28, thereby providing a rotational lock between the delivery member shield remover 46 and the delivery member protruding adjuster 28. Thus, when turning the delivery member shield remover 46 by gripping and turning the knob 50, the delivery member protruding adjuster 28 will also be turned and a required protruding length of the delivery member measured from the proximal end of the delivery member protruding adjuster, e.g. penetration depth, will be set as described above. When the required protruding length of the delivery member measured from the proximal end of the delivery member protruding adjuster, e.g. penetration depth, has been set, the delivery member shield 56 protecting the delivery member 60 may be removed in order to set the medicament delivery device ready for the user. The delivery member shield is then pulled in the proximal direction in relation to the medicament delivery device by gripping the knob 50. Because the ledges 54 are behind the delivery member shield 56 as seen from the proximal end, the delivery member shield 56 will also be pulled in the proximal direction. Thus the delivery member shield remover 46 and the delivery member shield 56 will be removed from the medicament delivery device.

In order to ensure that the delivery member shield remover 46 cannot fall out accidentally if for example the medicament delivery device is held with its proximal end downwards and/or if shaken or exposed to sudden forces, a friction enhancing element 68 is provided, FIGS. 6 and 7. It comprises a section 70, of the elongated body 48 of the delivery member shield remover 46 that is cut out and held in position by a number of flexible hinges 72, FIG. 7, on one side of the section. The outer surface of the section 70 is further arranged with a larger radius than the rest of the body such that the section 70, when introduced into the delivery member protruding adjuster 28 and the medicament delivery member cover 18, will be pressed against the inner surface of the medicament delivery member cover 18 with a certain flexible force, thereby providing a frictional lock of the delivery member shield remover 46 against the medicament delivery member cover 18. In this respect, it is to be understood that the friction enhancing mechanism may have other designs that can provide the desired and intended functions.

It is to be understood that the embodiment described above and shown in the drawings is to be regarded only as a non-limiting example of the invention and that it may be modified in many ways within the scope of the patent claims.

The invention claimed is:

1. A penetration depth adjusting mechanism for a medicament delivery device, which extends a longitudinal axis comprising:

a medicament delivery device housing having a proximal end and a distal end;

a medicament container arranged entirely inside of the medicament delivery device housing, wherein the medicament container is provided with a medicament delivery member;

a medicament delivery member cover coaxially arranged and movable in relation to the medicament delivery device housing; the penetration depth adjusting mechanism comprising:

a delivery member protruding adjuster operably connected to the medicament delivery member cover of the medicament delivery device and further comprises a signal generating mechanism arranged between the delivery member protruding adjuster and the medicament delivery member cover such that when the delivery member protruding adjuster is moved in relation to the medicament delivery member cover an audible and/or tactile and/or visual signal is generated, wherein the medicament delivery member cover together with the delivery member protruding adjuster are movable in relation to the medicament delivery device housing from a first position in which the medicament delivery member is surrounded by the medicament delivery member cover or by both the medicament delivery member cover and the delivery member protruding adjuster, to a second position in which the medicament delivery member is enabled to protrude a depth measured from a proximal end of the delivery member protruding adjuster, wherein the signal generating mechanism further comprises first signal elements arranged on the medicament delivery member cover of the medicament delivery device and second signal elements arranged on the delivery member protruding adjuster such that the first and second signal elements are able to interact with each other when displacement of the delivery member protruding adjuster occurs in relation to the medicament delivery member cover to thereby providing the audible and/or the tactile and/or the visual signal, and the first signal elements comprise at least one flexing element flexible in a direction generally perpendicular to a longitudinal axis of the penetration depth adjusting mechanism, and wherein the first signal elements further comprise at least one protrusion and the second signal elements comprise a plurality of recesses, wherein the plurality of recesses correspond to a plurality of medicament delivery member protruding depth setups, wherein, when the at least one protrusion is moved in position with one of the plurality of recesses, the at least one flexing element will cause a sudden movement of the at least one protrusion into the one of the plurality of recesses, causing an impact, thereby providing the audible and/or the tactile and/or the visual signal indicating that one of the medicament protruding depth setup of the plurality of medicament delivery member protruding depth setups has been set.

2. The penetration depth adjusting mechanism according to claim 1, wherein the proximal end of the delivery member protruding adjuster is provided with threads, wherein the threads are designed to interact with threads on a distal end of the medicament delivery member cover such that turning of the delivery member protruding adjuster in relation to the medicament delivery member cover will alter the delivery member protruding depth setups.

3. The penetration depth adjusting mechanism according to claim 1, wherein the delivery member protruding adjuster further comprises indicia indicative to the plurality of delivery member protruding depth setups.

4. The penetration depth adjusting mechanism according to claim 1, further comprising a tool operably connectable to the delivery member protruding adjuster for adjusting the delivery member protruding depth setups.

5. The penetration depth adjusting mechanism according to claim 4, wherein the tool is arranged connectable to a central passage of the delivery member protruding adjuster, wherein the tool and the central passage are arranged with cooperating rotation locking elements, wherein the cooperating rotation locking elements are designed to allow longitudinal movement between the tool and the delivery member protruding adjuster.

6. The penetration depth adjusting mechanism according to claim 5, wherein the tool is provided with gripping elements for gripping a delivery member shield surrounding the medicament delivery member placed inside the penetration depth adjusting mechanism, wherein the delivery member shield is removed when the tool is pulled from the delivery member protruding adjuster.

7. The penetration depth adjusting mechanism according to claim 6, wherein the tool is arranged with friction enhancing element arranged to interact with the delivery member protruding adjuster and/or the medicament delivery member cover for holding the tool.

8. A medicament delivery device comprising the penetration depth adjusting mechanism according to claim 1.

9. The medicament delivery device according to claim 8, wherein the medicament delivery device is an injection device.

10. The medicament delivery device according to claim 9, wherein the medicament delivery member is an injection needle.

11. The medicament delivery device according to claim 8, wherein a diameter of the medicament delivery member cover is less than a diameter of the medicament delivery device housing such that the medicament delivery member cover can move in a longitudinal direction in relation to the proximal end of the medicament delivery device housing.

12. The medicament delivery device according to claim 8, wherein the at least one flexing element comprises a bridge created by two parallel elongated cutouts in the signal generating mechanism.

13. The medicament delivery device according to claim 12, wherein the at least one flexing element comprises a tongue having a free end that is flexible in a radial direction.

14. The medicament delivery device according to claim 12, wherein the first signal elements further comprise the at least one protrusion and each recess of the plurality of recesses comprises a through-hole in the delivery member protruding adjuster.

15. The medicament delivery device according to claim 12, wherein the first signal elements further comprise the at least one protrusion and the at least one protrusion has a distinctive color that is visible through the one of the plurality of recesses when the at least one protrusion is moved in position with the one of the plurality of recesses.

16. The medicament delivery device according to claim 15, wherein the at least one protrusion comprises a truncated cone.

17. The medicament delivery device according to claim 16, wherein the plurality of recesses comprise a circular passage with straight side surfaces.

\* \* \* \* \*